US008288084B2

(12) United States Patent
Lee

(10) Patent No.: US 8,288,084 B2
(45) Date of Patent: Oct. 16, 2012

(54) COMPOSITION AND METHOD FOR FLUSHING AND COLD/CRYO PRESERVING ORGANS, TISSUES, AND CELLS

(75) Inventor: Hyung Taek Lee, Irvine, CA (US)

(73) Assignee: Revive Organtech, Inc., Irvine, CA (US)

( * ) Notice: Subject to any disclaimer, the term of this patent is extended or adjusted under 35 U.S.C. 154(b) by 377 days.

(21) Appl. No.: 12/660,710

(22) Filed: Mar. 3, 2010

(65) Prior Publication Data

US 2011/0008763 A1  Jan. 13, 2011

Related U.S. Application Data

(60) Provisional application No. 61/224,901, filed on Jul. 12, 2009.

(51) Int. Cl.
*A01N 1/00* (2006.01)
(52) U.S. Cl. .............................. 435/1.1; 435/1.2; 435/1.3
(58) Field of Classification Search .................. None
See application file for complete search history.

(56) References Cited

U.S. PATENT DOCUMENTS

| 4,415,556 | A | 11/1983 | Bretschneider |
| 4,798,824 | A | 1/1989 | Belzer et al. |
| 4,879,283 | A | 11/1989 | Belzer et al. |
| 4,920,044 | A | 4/1990 | Bretan, Jr. |
| 5,328,821 | A * | 7/1994 | Fisher et al. ............ 435/1.3 |
| 5,407,793 | A | 4/1995 | Del Nido et al. |
| 5,574,019 | A | 11/1996 | Segall et al. |
| 2004/0229203 | A1 | 11/2004 | Wiggins et al. |
| 2005/0100876 | A1 | 5/2005 | Khirabadi et al. |
| 2005/0250088 | A1 | 11/2005 | Boldt |
| 2006/0257842 | A1 | 11/2006 | Pettegrew et al. |
| 2008/0299535 | A1 | 12/2008 | Tokuda et al. |

OTHER PUBLICATIONS

International Preliminary Report on Patentability ; Feb. 7, 2011; World Intellectual Property Organization (WIPO) (International Bureau of); PCT/US2010/041704; 9 pages.
International Preliminary Report on Patentability; Jan. 17, 2012; World Intellectual Property Organization (WIPO) (International Bureau of); PCT/US2010/041704 ; 5 pages.
Collins et al; New Organ Preservation Solutions; Kidney Int. Suppl.; Oct. 1992; pp. 38:S197-202.

* cited by examiner

*Primary Examiner* — Sandra Saucier
(74) *Attorney, Agent, or Firm* — Fish & Richardson P.C.

(57) ABSTRACT

Materials and methods for preserving biological materials (e.g., organs, tissues, and cells) under cold or cryo conditions while reducing or minimizing damage to the materials.

22 Claims, 11 Drawing Sheets

(9 of 11 Drawing Sheet(s) Filed in Color)

White arrows, nuclear membrane
Yellow arrows, mitochondrial membrane
Red arrows, plasma membrane

COMPOSITION AND METHOD FOR FLUSHING AND COLD/CRYO PRESERVING ORGANS, TISSUES, AND CELLS

CROSS-REFERENCE TO RELATED APPLICATIONS

This application claims benefit of priority from U.S. Provisional Application Ser. No. 61/224,901, filed on Jul. 12, 2009.

TECHNICAL FIELD

This document relates to preserving biological materials, and more particularly to materials and methods for cold or cryo-preserving organs, tissues, and cells while reducing or minimizing damage to same.

BACKGROUND

Transplantation of organs such as liver, lung, kidney, heart, spleen, cornea, and pancreas has become a relatively routine mode of therapy for patients suffering from end stage organ disease. Despite major achievements in organ transplantation with regard to improved techniques, more specific immunosuppression, and better understanding and treatment of complications, preservation of organs prior to transplant still remains a critical issue.

Organ storage and preservation typically is done under hypothermic conditions in order to inhibit cellular metabolism and thereby suppress the rate of cellular deterioration. It also is important, however, to counteract effects of hypothermia (e.g., cell-swelling, reduced plasma membrane integrity, and enzyme leakage) in order to minimize organ damage. Some preservation solutions include one or more non-permeable components to reduce cell swelling, prevent intracellular acidosis, maintain plasma membrane integrity, and prevent expansion of the intracellular space. Some preservation solutions also contain antioxidants for scavenging oxygen radicals, and adenosine triphosphate (ATP) precursors to provide energy upon reperfusion.

A very commonly used organ preservation solution is the University of Wisconsin (UW) solution, also sold under the trade name VIASPAN™ by DuPont. This solution typically is considered to provide clinically good preservation of kidneys for up to 24 hours, livers for up to 12 hours, and hearts and lungs for about 5 hours of cold ischemic time. The major effective component of UW solution is 100 mM lactobionate, which has an insoluble nature that maintains the colloid oncotic pressure of the solution, delaying or preventing equilibration of the solution across the cell membrane and thus delaying cellular edema.

Several other types of organ preservation solutions also have been used to keep organs alive during transport from donor to recipient. These include EuroCollins (see, Collins et al. (1992) *Kidney Int. Suppl.* 38:S197-202), Marshall (or Ross-Marshall) solutions, HTK solution (marketed as CUSTODIOL® by Essential Pharmaceuticals, Newtown, Pa.), and CELSIOR®. EuroCollins solution contains high concentrations of potassium (110 mM), phosphate (60 mM), and glucose (180 mM). Ross-Marshall solutions have electrolytic compositions similar to those of EuroCollins solution, except that citrate replaces phosphate and mannitol replaces glucose. The citrate acts as a buffer and chelates with magnesium to form an impermeable molecule that helps stabilize the extracellular environment. Bretschneider HTK solution (see, e.g., U.S. Pat. No. 4,415,556) includes histidine as the buffer, tryptophan as a membrane stabilizer, and ketoglutarate as the energy substrate. CELSIOR® is an extracellular-type, low-viscosity solution that couples the impermeant, inert osmotic carrier from UW solution (using lactobionate and mannitol) and the strong buffer from Bretschneider HTK solution (using histidine).

SUMMARY

This document relates to improved materials and methods for cold/cryo preserving organs, tissues, and cells from humans or other animals. The solutions provided herein can permit cold preservation of viable organs, tissues, and cells for periods up to 72 hours, and possibly even longer. The solutions also can be used for cryopreserving organs, tissues, and cells for extended periods of time (e.g., up to two years), while maintaining their viability.

The methods provided herein can include contacting an organ, tissue, or cell with a solution containing particular concentrations and amounts of certain ingredients or types of ingredients. The materials and methods provided herein can, for example, reduce reperfusion injury to an organ during and/or following removal of the organ from a subject. Methods can include placing an organ in a solution containing one or more of the following: 5 to 40 mM sorbitol, 50 to 120 mM potassium D-gluconate, 10 to 40 mM D-saccharic acid (potassium salt), 15 to 30 mM potassium phosphate monobasic, 3 to 12 mM potassium citrate monobasic, 8 to 12 mM magnesium chloride, 2 to 7 mM D-(+)-fructose, 1 to 6 mM glutathione (reduced), 3 to 7 mM adenosine, 20 to 40 mM sodium hydroxide, 10 to 40 mM potassium hydroxide, 1 to 5 percent hydroxyethylstarch, 140 to 180 mEq/L potassium, 20 to 40 mEq/L sodium, 8 to 12 mEq/L magnesium, and 16 to 24 mEq/L chloride, and having a pH of 7.3 to 7.5 and an osmolality of 290 to 360 mOsm/Kg. The particular components can be included in amounts sufficient to maintain metabolic function and viability of the organs, tissues, and cells due to maintenance not only of plasma membrane integrity, but also nuclear and mitochondrial membrane integrity. By maintaining the integrity of these membranes at levels similar to those present under normal conditions, cold preservation of viable organs, tissues, and cells can be achieved for periods up to 72 hours, if not more. In some embodiments, the preservation solutions provided herein also are suitable for use in conjunction with a cryoprotectant [e.g., about 2, 5, 10, or 20 percent dimethyl sulfoxide (DMSO)] to provide for cryopreservation of viable organs, tissues, and cells for periods of two years or longer.

It is to be noted that other than in the working examples or where otherwise indicated, all numbers used herein with regard to quantities/concentrations of solution components, as well as solution conditions (e.g., pH and osmolality), should be understood as modified in all instances by the term "about."

In one aspect, this document features a composition comprising 5 to 40 mM sorbitol; 50 to 120 mM potassium D-gluconate; 10 to 40 mM D-saccharic acid (potassium salt); 15 to 30 mM potassium phosphate monobasic; 3 to 12 mM potassium citrate monobasic; 8 to 12 mM magnesium chloride; 2 to 7 mM D-(+)-fructose; 1 to 6 mM glutathione (reduced); 3 to 7 mM adenosine; 20 to 40 mM sodium hydroxide; 10 to 40 mM potassium hydroxide; 140 to 180 mEq/L potassium; 20 to 40 mEq/L sodium; 8 to 12 mEq/L magnesium; and 16 to 24 mEq/L chloride, wherein the composition has a pH of 7.3 to 7.5 and an osmolality of 290 to 360 mOsm/Kg. The composition can comprise 145 mEq/L potassium. The composition can comprise sodium and chloride at a ratio of 3:2 sodium:

chloride. The composition can comprise 10 mM magnesium chloride. The composition can contain no sulfate. The composition can further comprise 10 percent dimethyl sulfoxide (DMSO), or 1 to 5 percent hydroxyethylstarch.

In some cases, the composition can comprise 30 mM sorbitol; 73 mM potassium D-gluconate; 20 mM D-saccharic acid (potassium salt); 25 mM potassium phosphate monobasic; 5 mM potassium citrate monobasic; 10 mM magnesium chloride; 5 mM D-(+)-fructose; 3 mM glutathione (reduced); 5 mM adenosine; 30 mM sodium hydroxide; 23 mM potassium hydroxide; 145 mEq/L potassium; 30 mEq/L sodium; 10 mEq/L magnesium; and 20 mEq/L chloride, wherein the composition has a pH of 7.4 and an osmolality of 320 mOsm/Kg. The composition can further comprise 10 percent DMSO, or 5 percent hydroxyethylstarch.

In another aspect, this document features a method for preserving a cell, comprising contacting the cell with a composition as provided herein, and placing the cell at a temperature of 0 to 1° C. The method can further comprise storing the cell at 0 to 1° C. for up to 72 hours. The cell can be a liver, kidney, spleen, pancreas, heart, lung, small bowel, eye, or skin cell. The method of claim 10, wherein the cell can be within a liver, kidney, spleen, pancreas, heart, lung, small bowel section, eye, or skin section. The cell can be a mammalian cell (e.g., a human cell). The composition can comprise any or all of 5 to 40 mM sorbitol; 50 to 120 mM potassium D-gluconate; 10 to 40 mM D-saccharic acid (potassium salt); 15 to 30 mM potassium phosphate monobasic; 3 to 12 mM potassium citrate monobasic; 8 to 12 mM magnesium chloride; 2 to 7 mM D-(+)-fructose; 1 to 6 mM glutathione (reduced); 3 to 7 mM adenosine; 20 to 40 mM sodium hydroxide; 10 to 40 mM potassium hydroxide; 1 to 5 percent hydroxyethylstarch; 10 percent DMSO; 140 to 180 mEq/L potassium; 20 to 40 mEq/L sodium; 8 to 12 mEq/L magnesium; and 16 to 24 mEq/L chloride, and can have a pH of 7.3 to 7.5 and an osmolality of 290 to 360 mOsm/Kg.

In another aspect, this document features a method for cryopreserving a cell, comprising contacting the cell with a composition as provided herein (e.g., a composition comprising 5 to 40 mM sorbitol; 50 to 120 mM potassium D-gluconate; 10 to 40 mM D-saccharic acid (potassium salt); 15 to 30 mM potassium phosphate monobasic; 3 to 12 mM potassium citrate monobasic; 8 to 12 mM magnesium chloride; 2 to 7 mM D-(+)-fructose; 1 to 6 mM glutathione (reduced); 3 to 7 mM adenosine; 20 to 40 mM sodium hydroxide; 10 to 40 mM potassium hydroxide; 10 percent DMSO; 1 to 5 percent hydroxyethylstarch; 140 to 180 mEq/L potassium; 20 to 40 mEq/L sodium; 8 to 12 mEq/L magnesium; and 16 to 24 mEq/L chloride, and having a pH of 7.3 to 7.5 and an osmolality of 290 to 360 mOsm/Kg), and placing the cell at a temperature of about −196° C. The method can further comprise storing the cell at −196° C. for up to two years. The cell can be a liver, kidney, spleen, pancreas, heart, lung, small bowel, eye, or skin cell. The cell can be within a liver, kidney, spleen, pancreas, heart, lung, small bowel section, eye, or skin section. The cell can be a mammalian cell (e.g., a human cell). The composition can comprise 30 mM sorbitol; 73 mM potassium D-gluconate; 20 mM D-saccharic acid (potassium salt); 25 mM potassium phosphate monobasic; 5 mM potassium citrate monobasic; 10 mM magnesium chloride; 5 mM D-(+)-fructose; 3 mM glutathione (reduced); 5 mM adenosine; 30 mM sodium hydroxide; 23 mM potassium hydroxide; 10 percent DMSO; 5 percent hydroxyethylstarch; 145 mEq/L potassium; 30 mEq/L sodium; 10 mEq/L magnesium; and 20 mEq/L chloride, and can have a pH of 7.4 and an osmolality of 320 mOsm/Kg.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
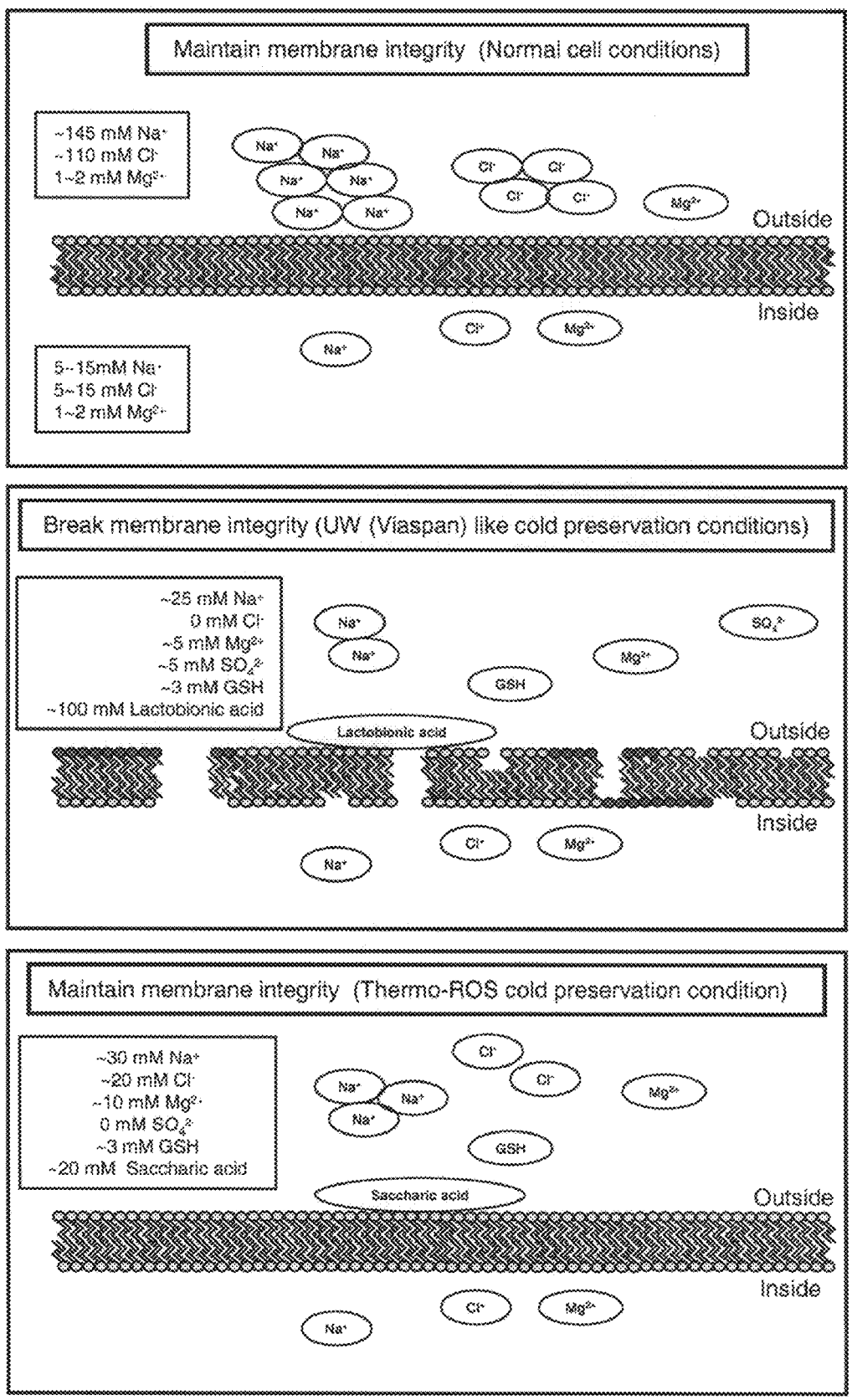
FIG. 1 is a schematic depicting potential cellular conditions when storing/preserving organs in a solution containing optimal concentrations of sodium, chloride, magnesium, sulfonic acid, saccharic acid, and glutathione (GSH). Top panel, depiction of normal cellular conditions; middle panel, depiction of conditions using a UW-like solution for organ preservation; bottom panel, depiction of conditions using a Thermo-ROS like solution for organ preservation.

This document provides physiologically acceptable preservation solutions that can be used for cold or cryopreservation of organs, tissues, and cells. Use of the solutions provided herein may provide a three- to six-fold increase in preservation time over known preservation solutions. In general, the preservation solutions provided herein can contain one or more of the following: 5 to 40 mM (e.g., 5, 10, 15, 20, 25, 30, 35, or 40 mM, or any range there between) sorbitol, 50 to 120 mM (e.g., 50, 55, 60, 65, 70, 75, 80, 85, 90, 95, 100, 105, 110, 115, or 120 mM, or any range there between) potassium D-gluconate, 10 to 40 mM (e.g., 10, 15, 20, 25, 30, 35, or 40 mM, or any range there between) D-saccharic acid, potassium salt, 15 to 30 mM (e.g., 15, 20, 25, or 30 mM, or any range there between) potassium phosphate monobasic, 3 to 12 mM (e.g., 3, 4, 5, 6, 7, 8, 9, 10, 11, or 12 mM, or any range there between) potassium citrate monobasic, 8 to 12 mM (e.g., 8, 9, 10, 11, or 12 mM, or any range there between) magnesium chloride, 2 to 7 mM (e.g., 2, 3, 4, 5, 6, or 7 mM, or any range there between) D-(+)-fructose, 1 to 6 mM (e.g., 1, 2, 3, 4, 5, or 6 mM, or any range there between) reduced glutathione, 3 to 7 mM (e.g., 3, 4, 5, 6, or 7 mM, or any range there between) adenosine, 20 to 40 mM (e.g., 20, 25, 30, 35, or 40 mM, or any range there between) sodium hydroxide, 10 to 40 mM (e.g., 10, 15, 20, 25, 30, 35, or 40 mM, or any range there between) potassium hydroxide, 1 to 5 percent (e.g., 1, 2, 3, 4, or 5 percent, or any range there between) hydroxyethyl-starch, 140 to 180 mEq/L (e.g., 140, 145, 150, 155, 160, 165, 170, 175, or 180 mEq/L, or any range there between) potassium, 20 to 40 mEq/L (e.g., 20, 25, 30, 35, or 40 mEq/L, or any range there between) sodium, 8 to 12 mEq/L (e.g., 8, 9, 10, 11, or 12 mEq/L, or any range there between) magnesium, 16 to 24 mEq/L (e.g., 16, 18, 20, 22, or 24 mEq/L, or any range there between) chloride, and no sulfate. Further, the solutions can have a pH of 7.3 to 7.5 (e.g., 7.3, 7.35, 7.4, 7.45, 7.5, or any range there between), and an osmolality of 290 to 360 mOsm/Kg (e.g., 290, 295, 300, 305, 310, 315, 320, 325, 330, 335, 340, 345, 350, 355, or 360 mOsm/Kg, or any range there between). The concentrations, pH, and osmolality can be selected to maintain the metabolic function and viability of organs, tissues, and cells, due to maintenance of plasma membrane integrity to a level similar to or the same as plasma membrane integrity observed under normal conditions. The solutions also can permit cold preservation of viable organs and tissues for up to about 72 hours. Further, the effectiveness of any physiologically acceptable preservation buffer solution may be improved by adjusting the amount of any one or more of the above components.

As used herein, a "physiologically acceptable solution" refers to a solution that can minimize or prevent hypothermia-induced cell swelling, intracellular acidosis, expansion of extracellular space, and injury from oxygen free radicals, and also can provide substrates for regenerating high energy phosphate compounds. In general, a physiologically acceptable solution will contain an effective impermeant to prevent, minimize, or reduce hypothermic induced cell swelling. Examples of impermeants that can be included in the physiologically acceptable solutions provided herein include, without limitation, lactobionate, raffinose, hydroxyethyl starch (HES), gluconate, saccharate, and sorbitol.

Physiologically acceptable solutions also typically include a hydrogen ion buffer, such as for example, a phosphate. Adenosine (an ATP precursor), as well as fructose and/or citrate (which provide precursors for regeneration of high energy phosphate compounds) also may be included. Other ingredients that may be included in a physiologically acceptable solution include, without limitation, inorganic salts such as $MgCl_2$, reducing agents such as glutathione, and antibiotics such as penicillin and/or gentamycin. Further, the preservation solutions provided herein can have an osmolality in the range of about 290 to about 360, and a neutral pH (e.g., in the range of 7.3 to 7.5).

Physiologically acceptable solutions upon which the preservation solutions provided herein may be based include, without limitation, those disclosed in U.S. Pat. Nos. 4,415,556; 4,920,044; 4,798,824; 4,879,783; 5,328,821; and 5,407,793, the disclosures of which are incorporated herein by reference. The compositions of two previously known solutions are presented in Table 1.

TABLE 1

Compositions of V-7 solution and UW solution

| V-7 solution composition range (preferred) | UW solution |
|---|---|
| Gluconate (K salt)—30-120 mM (60 mM) | Potassium—125 mM |
| Saccharate (K salt)—30-120 mM (60 mM) | Sodium—25 mM |
| Potassium phosphate monobasic—25-30 mM (25 mM) | Magnesium—5 mM |
| Sodium succinate—1-3 mM (2 mM) | Lactobionate—100 mM |
| Magnesium sulfate—3-6 mM (5 mM) | Phosphate—25 mM |
| Magnesium chloride—1-3 mM (2 mM) | Sulfate—5 mM |
| Potassium bicarbonate—1-3 mM (2 mM) | Raffinose—30 mM |
| Glucose—2-4 mM (2 mM) | Adenosine—5 mM |
| Fructose—2-4 mM (2 mM) | Allopurinol—1 mM |
| Glutathione (reduced)—3-6 mM (6 mM) | Glutathione—3 mM |
| Ascorbic acid (K salt)—2-10 mM (5 mM) | Insulin—100 U/L |
| Adenosine—3-5 mM (5 mM) | Dexamethasone—8 mg/L |
| Antibiotics (gentamycin or penicillin)—µM amounts | Hydroxyethyl starch—50 g/L |
| Deferoxamine mesylate—µmolar amounts | Bactrim 0.5 ml/L |
| pH 7.3-7.5 (7.4) | pH 7.4 |
| Osmolality 320-360 mOsm/Kg (340 mOsm/Kg) | Osmolality 320 mOsm/kg |

An exemplary list of the ingredients for a preservation solution as provided herein is presented in Table 2. A range for the amount of each ingredient is given, with the exact formulation of a particularly useful solution provided in parentheses. The solution having this exact formulation is hereinafter referred to as "Thermo-ROS solution."

TABLE 2

Composition of exemplary preservation solutions (Thermo-ROS)

| | |
|---|---|
| Sorbitol | 5 to 40 mM (30 mM) |
| Potassium D-gluconate | 50 to 120 mM (73 mM) |
| D-saccharic acid, potassium salt | 10 to 40 mM (20 mM) |
| Potassium phosphate monobasic | 15 to 30 mM (25 mM) |
| Potassium citrate monobasic | 3 to 12 mM (5 mM) |
| Magnesium chloride | 8 to 12 mM (10 mM) |
| D-(+)-fructose | 2 to 7 mM (5 mM) |
| Glutathione, reduced | 1 to 6 mM (3 mM) |
| Adenosine | 3 to 7 mM (5 mM) |
| Sodium hydroxide | 20 to 40 mM (30 mM) |
| Potassium hydroxide | 10 to 40 mM (23 mM) |
| Hydroxyethylstarch | 1 to 5 percent (5 percent) |
| Potassium | 140 to 180 mEq/L (145 mEq/L) |
| Sodium | 20 to 40 mEq/L (30 mEq/L) |
| Magnesium | 8 to 12 mEq/L (10 mEq/L) |
| Chloride | 16 to 24 mEq/L (20 mEq/L) |
| Sulfate | 0 mEq/L |
| pH | 7.3 to 7.5 (7.4) |
| Osmolality | 290 to 360 mEq/L (320 mEq/L) |

Thermo-ROS and the related solutions provided by this document were developed to address at least the following points.

Intracellular and extracellular concentrations of electrolytes differ. For example, extracellular conditions typically include about 145 mM sodium, about 110 mM chloride, about 5 mM potassium, and about 0.5 mM magnesium, while intracellular conditions typically include about 5 to 15 mM sodium, about 5 to 15 mM chloride, about 140 mM potassium, and about 1 to 2 mM magnesium. These electrolytes have important roles in maintaining the stability and integrity of the cell membrane.

Intracellular and extracellular concentrations of larger molecules (e.g., proteins, lipids, and polysaccharides) also differ. In particular, higher concentrations of such molecules within the cell as compared to outside the cell lead to an imbalance in osmolality between the inside and outside of the cell. To maintain optimal osmolality, the cell uses a $Na^+$—$K^+$ ATPase pump that pumps three $Na^+$ ions out of the cell and two $K^+$ ions into the cell. Due to the $Na^+$—$K^+$ ATPase pump, the interior of the cell has a higher concentration of $K^+$ (about 140 mM) than the exterior of the cell, which typically has a $K^+$ level of about 5 mM. To counter this imbalance in $K^+$ levels between the interior and exterior, the cell has a potassium leak channel through which potassium is slowly leaked from the cell. This potassium leakage generates a slightly positive charge outside the cell and a negative charge inside the plasma membrane. The different charges inside and outside the plasma membrane result in the membrane potential. The membrane potential has very important roles in membrane integrity and cell viability. For example, the plasma membrane contains many different types and orientations of proteins, lipids, and polysaccharides. If the membrane potential is modified between the outside and the inside of the plasma membrane, the types and orientations of proteins, lipids, and polysaccharides in the membrane may be altered, resulting in damage to and possible malfunction of the membrane.

The cold temperatures associated with flushing and storage during organ preservation result in blockage of the $Na^+$—$K^+$ ATPase pump and the $K^+$ leak channel. Thus, under such cold conditions, the plasma membrane potential and integrity are not easily maintained. UW solution is an intracellular type of cold organ preservation solution that contains 125 mM $K^+$ ion. Thus, UW solution has a slightly lower concentration of $K^+$ ions than the intracellular area, which typically contains about 140 mM $K^+$ ions. When UW solution is used for organ flushing and storage, the plasma membrane integrity is broken due to the slightly low $K^+$ concentrations. This may result in cellular damage and loss of viability and function during the cold preservation time. In contrast, an organ preservation solution having a $K^+$ ion concentration of about 145 mM (i.e., slightly higher than the intracellular $K^+$ ion concentration) may maintain plasma membrane integrity due to maintenance of membrane potential under cold storage conditions.

In addition, the ratios of some ions (e.g., sodium and chloride) may be important for maintaining plasma, nuclear, and mitochondrial membrane integrity. UW solution contains 25 mM sodium, but does not contain chloride. Sodium is present in the extracellular area (about 150 mM), as is chloride (about 110 mM), giving an extracellular sodium:chloride ratio of about 3:2. Based at least in part on the experimental results presented herein, a ratio of about 3:2 sodium:chloride (e.g., about 2.5:2, about 2.75:2, or about 3:2 sodium:chloride) may be important for maintaining membrane integrity and stability.

Magnesium also may play an important role in membrane stability. In addition, the effect of magnesium cations (e.g., $Mg^{2+}$) may depend on the anions with which they are paired. Different ions may react differently and/or selectively with the membrane, increasing or decreasing its stability. For example, $MgCl.6H_2O$ can increase membrane stability at low concentrations but decrease stability at higher concentrations, on both sides of the amnion. $MgSO_4$ has been shown to increase membrane stability on the maternal side and decrease stability on the fetal side.

A schematic depicting potential benefits of storing/preserving organs in solutions containing optimal concentrations of sodium, chloride, magnesium, sulfonic acid, saccharic acid, and glutathione (GSH) is shown in FIG. 1. The top panel depicts normal cellular conditions. The middle panel depicts cellular conditions when a UW-like solution is used for organ preservation, and the bottom panel depicts cellular conditions when a thermo-ROS like solution is used for organ preservation.

Figure 2:
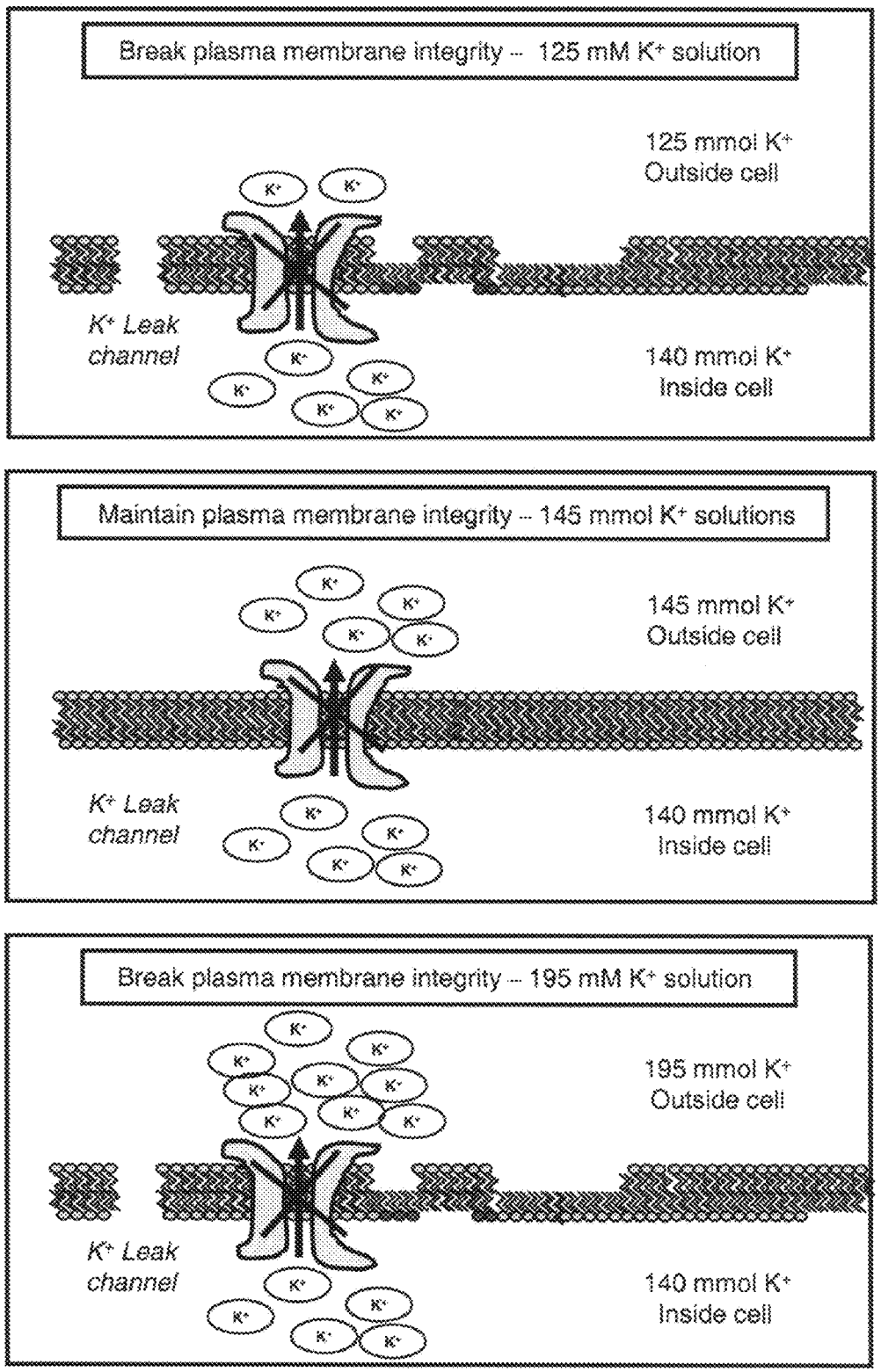
FIG. 2 is a schematic depicting potential cellular conditions when storing/preserving organs in a solution containing an optimal concentration of potassium ions. Top panel, depiction of cellular conditions when using a UW-like solution (125 mM K$^+$) for organ preservation; middle panel, depiction of cellular conditions when using a Thermo-ROS like solution (145 mM K$^+$) solution for organ preservation; bottom panel, depiction of cellular conditions when using a V-7 like solution (195 mM K$^+$) solution for organ preservation.

A schematic depicting potential benefits of storing/preserving organs in solutions containing optimal concentrations of potassium ion is shown in FIG. 2. The top panel depicts cellular conditions when a UW-like solution containing 125 mM $K^+$ is used for organ preservation. The middle panel depicts cellular conditions when a Thermo-ROS like solution containing 145 mM $K^+$ is used for organ preservation, and the bottom panel depicts cellular conditions when a V-7 like solution containing 195 mM $K^+$ is used for organ preservation.

Preservation solutions also can include components such as citrate and fructose, which are involved in the glycolytic pathway and the Krebs cycle, and can be included to provide energy sources via generation of ATP. Such components also can be important for maintaining cell viability under anaerobic cold preservation conditions. It is noted that when cryopreservation is desired, components such as glutathione, fructose, citrate, and adenosine may be omitted from the preservation solution.

In addition, preservation solutions can include impermeant components to maintain optimal osmolality. For example, UW solution contains HES (a polysaccharide) and lactobionic acid (a disaccharide). Other types of saccharides (e.g., monosaccharides such as saccharic acid and sorbitol) also may be included, as described in the Examples herein. Without being bound by a particular mechanism, monosaccharides may be particularly useful due to, e.g., their smaller size, or the ability to better interact with and stabilize the extracellular membrane.

Given the above, the Thermo-ROS solution provided herein has at least the following special features. It is noted that other solutions provided herein also have some or all of these features.

1) Its osmolality is the same as or similar to that of extracellular fluid (290 to 360 mOsm/Kg).

2) It has high potassium ion content, approximating that of the intracellular milieu (140 to 180 mEq/L).

3) It has low sodium ion content, approximating very low extracellular sodium ion concentrations (20 to 40 mEq/L).

4) It has low chloride ion content, approximating very low extracellular chloride ion concentrations (16 to 24 mEq/L). Chloride ions are supplied only by magnesium chloride.

5) It has a sodium:chloride ratio of about 3:2.

6) It has high magnesium ion content, approximating relatively high extracellular magnesium ion concentrations (8 to 12 mEq/L). Magnesium is supplied only by magnesium chloride.

7) It is devoid of calcium.

8) It is rich in antioxidant (1 to 6 mM glutathione).

9) It is rich in an energy source and ATP precursor (3 to 7 mM adenosine).

10) It includes the acid generating substrates citrate (3 to 12 mM) and saccharic acid (10 to 40 mM).

11) It contains a plasma expander—hydroxyethylstarch (1 to 5 percent) and other high molecular weight monosaccharide compounds—gluconate (50 to 120 mM), saccharic acid (10 to 40 mM), and sorbitol (about 5 to 40 mM).

12) It has the same pH as extracellular fluid (7.3 to 7.5).

13) It is devoid of magnesium sulfate.

14) It includes low concentrations (2 to 7 mM) of fructose, which is used in glycolysis.

15) Its pH is adjusted with sodium hydroxide (20 to 40 mM) and potassium hydroxide (10 to 40 mM).

The preservation solutions provided herein can be prepared in any suitable manner. Typically, the ingredients are added to distilled or deionized water. After all ingredients are dissolved, the pH can be adjusted (e.g., with 5 M sodium hydroxide and/or 5 M potassium hydroxide). In some embodiments, 30 mM of sodium hydroxide can be added per liter of solution, followed by 23 mM of potassium hydroxide for pH adjustment. A particular order of addition for the various solution ingredients may be beneficial in certain circumstances. For example, it may be useful to delay adding components that are not stable for long periods in an aqueous environment, such as reduced glutathione. In such cases, the stable ingredients may be mixed together during initial preparation of the solution, and the sensitive materials can be added just prior to use of the solution. In addition, it should be understood that a preservation solution may be provided as a concentrate to be diluted with distilled or deionized water just prior to use.

The invention will be further described in the following examples, which do not limit the scope of the invention described in the claims.

EXAMPLES

Experiments were conducted in which rat livers and kidneys were incubated in fifty-eight different types of preservation solutions, with varying ion contents, under the oxygen tension of ambient air and at the temperature of melting ice (0 to 1° C.). Organs incubated in Thermo-ROS under such conditions maintained high viability and functionality for up to 72 hours.

Viability and membrane integrity of cells were evaluated as follows. After storage in preservation solutions at 0 to 1° C. under the oxygen tension of ambient air for the designated lengths of time, organs were placed in 10% neutralization solution (Formalin) for tissue fixation. After 24 hours of fixation, Hematoxylin and Eosin (H&E) specimens were prepared. Samples were viewed using Leica bright microscopy with SPOT digital camera evaluation, and cell viability and membrane integrity were visually determined.

Plasma membrane, nuclear membrane, and mitochondrial membrane integrity were evaluated as follows. Organs were stored in preservation solutions at 0 to 1° C. for the designated length of time, under the oxygen tension of ambient air. After storage, organs were placed in a 2.5% glutaraldehyde solution for tissue fixation. After 24 hours of fixation, electron microscopy specimens were prepared. Samples were viewed using transmission electron microscopy (TEM), and integrity of the various membranes was visually determined.

Viability and membrane integrity of cryopreserved cells were evaluated as follows. Thermo-ROS containing 10% DMSO was used to preserve rat livers. Livers were removed from the animals, placed in the cryopreservation solution, and immediately transferred to a −20° C. freezer. After storage for three days, samples were removed from the freezer and immediately placed in a 37° C. water bath to defrost the tissues. Once defrosted, samples were placed in 10% neutralization solution (Formalin) for tissue fixation. After 24 hours of fixation, H&E specimens were prepared. Samples were viewed using Leica bright microscopy with SPOT digital camera evaluation, and cell viability and membrane integrity were visually determined.

Rat kidney transplant experiments were conducted as follows. Eight Lewis, male rats (four donors and four recipients) weighing 250 to 300 g were used. The right kidney was removed from each donor and flushed with either cold UW solution (n=2) or Thermo-ROS (n=2), followed by storage in an ice cold chamber. After storage for the designated length of time (about 34 hours for UW solution and about 37 hours for Thermo-ROS), kidneys were reflushed with cold saline solution and transplanted into the recipients, with anastomosis at each recipient's abdominal aorta, vein, and ureter. Survival of recipient animals was monitored. To evaluate the function of the transplanted kidneys, blood samples were taken from recipients, and creatinine and blood urea nitrogen concentrations were measured by a blood chemistry lab (Antech Diagnostics, Irvine, Calif.).

Example 1

Comparison Studies Using Different ROS Solutions

Organs (liver and kidney) from rats were placed in different types of ROS solutions and maintained at 0 to 1° C. Tissue viability was evaluated after 24 and 48 hours of cold preservation. ROS compositions are listed in Tables 3A, 4A, 5A, 6A, 7A, and 8A, and experimental results are shown in Tables 3B, 4B, 5B, 6B, 7B, and 8B, and in FIGS. 3-8. Tissue viability was evaluated by H&E staining of the stored specimens.

Based on the data presented in Tables 3B-8B and FIGS. 3-8, the optimal preservation solution contains 30 mM sorbitol, 73 mM potassium D-gluconate, 20 mM saccharic acid (potassium salt), 25 mM potassium phosphate monobasic, 5 mM potassium citrate monobasic, 0 mM magnesium sulfate, 10 mM magnesium chloride, 5 mM D-(+)-fructose, 3 mM glutathione (reduced), 5 mM adenosine, 30 mM sodium hydroxide, 23 mM potassium hydroxide, 145 mM potassium, 30 mM sodium, 10 mM magnesium, 20 mM chloride, and 0 mM sulfonic acid, and has an osmolality of 320 mOsm/Kg and pH 7.40.

TABLE 3A

Figure 3:
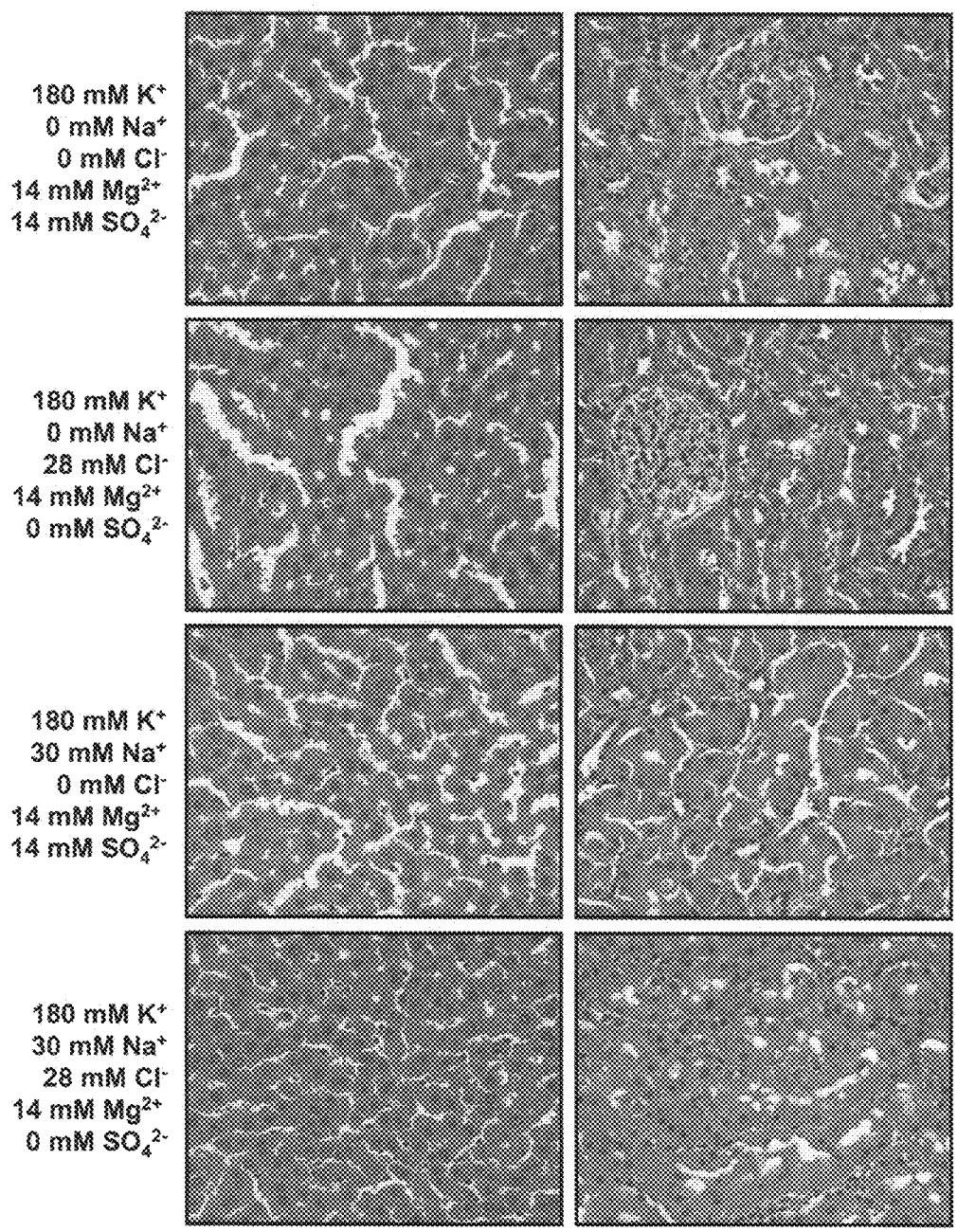
FIG. 3. is a series of pictures of rat liver and kidney tissue sections from a comparison study using ROS solutions 3, 4, 5, and 6, which contained the indicated concentrations of K$^+$, Na$^+$, Cl$^-$, Mg$^{2+}$ and SO$_4^{2-}$ ions. Samples were subjected to cold preservation for 24 hours and evaluated with hematoxylin and eosin (H&E) staining.

Compositions of ROS 3, 4, 5, and 6 (used in FIG. 3)

| | ROS-3 | ROS-4 | ROS-5 | ROS-6 |
|---|---|---|---|---|
| Potassium D-gluconate* | 61 | 61 | 91 | 91 |
| Saccharic acid potassium salt | 30 | 30 | 30 | 30 |
| Potassium phosphate monobasic | 25 | 25 | 25 | 25 |
| Potassium citrate monobasic | 5 | 5 | 5 | 5 |
| Magnesium sulfate | 14 | 0 | 14 | 0 |
| Magnesium chloride | 0 | 14 | 0 | 14 |
| D-(+)-Fructose | 2 | 2 | 2 | 2 |
| Adenosine | 3 | 3 | 3 | 3 |
| Sodium hydroxide | 0 | 0 | 30 | 30 |
| Potassium hydroxide | 59 | 59 | 29 | 29 |
| Potassium | 180 | 180 | 180 | 180 |
| Sodium | 0 | 0 | 30 | 30 |
| Magnesium | 14 | 14 | 14 | 14 |
| Chloride | 0 | 28 | 0 | 28 |
| Sulfonic acid | 14 | 0 | 14 | 0 |
| Osmolality (mOsm/Kg) | 270 | 297 | 330 | 363 |
| pH | 7.40 | 7.40 | 7.40 | 7.40 |

*all concentrations mM

TABLE 3B

Liver and kidney viability after 24 hours of cold preservation in ROS-3, ROS-4, ROS-5, or ROS-6 (evaluated by H&E staining; see FIG. 3)

| | $Na^{+}$* | $Cl^{-}$ | $Mg^{2+}$ | $SO_4^{2-}$ | Liver | Kidney |
|---|---|---|---|---|---|---|
| ROS-3 | 0 | 0 | 14 | 14 | 30% | 20% |
| ROS-4 | 0 | 28 | 14 | 0 | 30% | 40% |
| ROS-5 | 30 | 0 | 14 | 14 | 20% | 20% |
| ROS-6 | 30 | 28 | 14 | 0 | 60% | 50% |

*all concentrations mM

TABLE 4A

Figure 4:
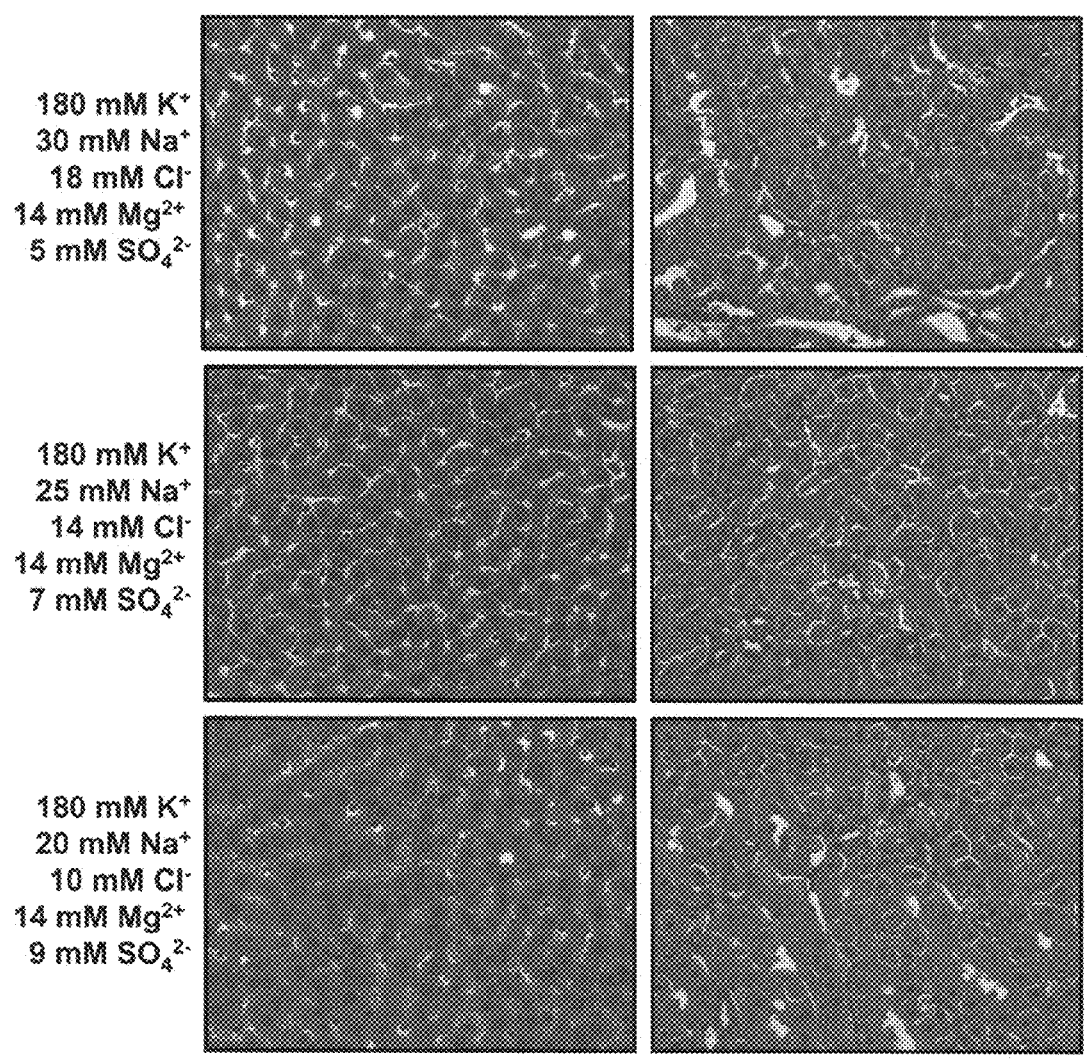
FIG. 4 is a series of pictures of rat liver and kidney tissue sections from a comparison study using ROS solutions 8, 9, and 10, which contained the indicated concentrations of K$^+$, Na$^+$, Cl$^-$, Mg$^{2+}$ and SO$_4^{2-}$ ions. Samples were subjected to cold preservation for 24 hours and evaluated with H&E staining.

Compositions of ROS solutions 8, 9, and 10 (used in FIG. 4)

| | ROS-8 | ROS-9 | ROS-10 |
|---|---|---|---|
| Potassium D-Gluconate* | 86.6 | 83 | 78 |
| Saccharic acid potassium salt | 30 | 30 | 30 |
| Potassium phosphate monobasic | 25 | 25 | 25 |
| Potassium citrate monobasic | 5 | 5 | 5 |
| Magnesium sulfate | 5 | 7 | 9 |
| Magnesium chloride | 9 | 7 | 5 |
| D-(+)-Fructose | 2 | 2 | 2 |
| Glutathione reduced | 3 | 3 | 3 |
| Adenosine | 3 | 3 | 3 |
| Sodium hydroxide | 30 | 25 | 20 |
| Potassium hydroxide | 33.4 | 37 | 42 |
| Potassium | 180 | 180 | 180 |
| Sodium | 30 | 25 | 20 |
| Magnesium | 14 | 14 | 14 |
| Chloride | 18 | 14 | 10 |
| Sulfonic acid | 5 | 7 | 9 |
| Osmolality (mOsm/Kg) | 329 | 327 | 314 |
| pH | 7.40 | 7.40 | 7.40 |

*all concentrations mM

TABLE 4B

Liver and kidney viability after 24 hours of cold preservation in ROS-8, ROS-9, or ROS-10 (evaluated by H&E staining; see FIG. 4)

| | $Na^{+}$* | $Cl^{-}$ | $Mg^{2+}$ | $SO_4^{2-}$ | Liver | Kidney |
|---|---|---|---|---|---|---|
| ROS-8 | 30 | 18 | 14 | 5 | 80% | 70% |
| ROS-9 | 25 | 14 | 14 | 7 | 70% | 30% |
| ROS-10 | 20 | 10 | 14 | 9 | 50% | 30% |

*all concentrations mM

TABLE 5A

Figure 5:
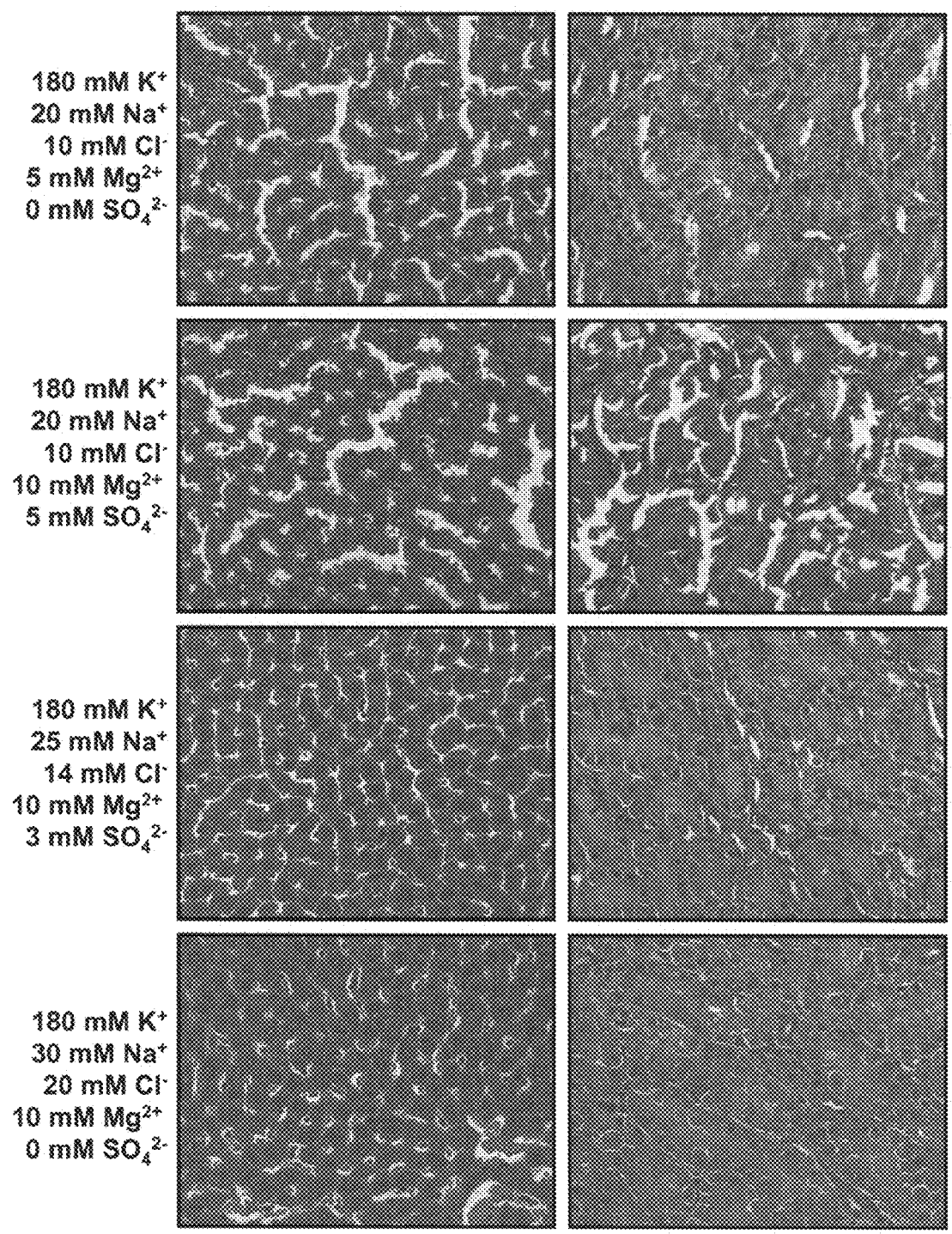
FIG. 5 is a series of pictures of rat liver and kidney tissue sections from a comparison study using ROS solutions 14, 16, 18, and 20, which contained the indicated concentrations of K$^+$, Na$^+$, Cl$^-$, Mg$^{2+}$ and SO$_4^{2-}$ ions. Samples were subjected to cold preservation for 24 hours and evaluated with H&E staining.

Compositions of ROS 14, 16, 18, and 20 (used in FIG. 5)

| | ROS-14 | ROS-16 | ROS-18 | ROS-20 |
|---|---|---|---|---|
| Potassium D-gluconate* | 78.6 | 78 | 82.6 | 87.4 |
| Saccharic acid potassium salt | 30 | 30 | 30 | 30 |
| Potassium phosphate monobasic | 25 | 25 | 25 | 25 |
| Potassium citrate monobasic | 5 | 5 | 5 | 5 |
| Magnesium sulfate | 0 | 5 | 3 | 0 |
| Magnesium chloride | 5 | 5 | 7 | 10 |
| D-(+)-Fructose | 2 | 2 | 2 | 2 |
| Adenosine | 3 | 3 | 3 | 3 |
| Glutathione reduced | 3 | 3 | 3 | 3 |
| Sodium hydroxide | 20 | 20 | 25 | 30 |
| Potassium hydroxide | 41.8 | 42 | 37.4 | 32.6 |
| Potassium | 180 | 180 | 180 | 180 |
| Sodium | 20 | 20 | 25 | 30 |
| Magnesium | 5 | 10 | 10 | 10 |
| Chloride | 10 | 10 | 14 | 20 |
| Sulfonic acid | 0 | 5 | 3 | 0 |
| Osmolality (mOsm/Kg) | 312 | 305 | 317 | 339 |
| pH | 7.41 | 7.40 | 7.40 | 7.40 |

*all concentrations mM

TABLE 5B

Liver and kidney viability after 24 hours of cold preservation in ROS-14, ROS-16, ROS-18, or ROS-20 (evaluated by H&E staining; see FIG. 5)

| | $Na^{+}$* | $Cl^{-}$ | $Mg^{2+}$ | $SO_4^{2-}$ | Liver | Kidney |
|---|---|---|---|---|---|---|
| ROS-14 | 20 | 10 | 5 | 0 | 30% | 60% |
| ROS-16 | 20 | 10 | 10 | 5 | 30% | 10% |
| ROS-18 | 25 | 14 | 10 | 3 | 80% | 40% |
| ROS-20 | 30 | 20 | 10 | 0 | 90% | 70% |

*all concentrations mM

TABLE 6A

Figure 6:
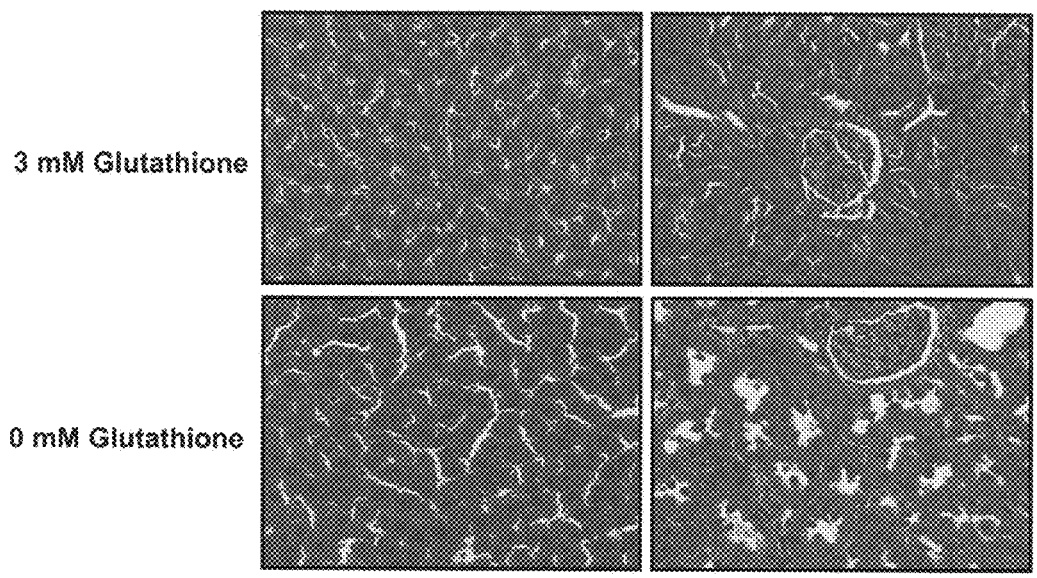
FIG. 6 is a series of pictures of rat liver and kidney tissue sections from a comparison study using ROS solutions 20 and 21, containing the indicated concentrations of the antioxidant glutathione (GSH). Samples were subjected to cold preservation for 24 hours and evaluated with H&E staining.

Compositions of ROS 20 and 21 (used in FIG. 6)

| | ROS-20 | ROS-21 |
|---|---|---|
| Potassium D-gluconate* | 87.4 | 91 |
| Saccharic acid potassium salt | 30 | 30 |
| Potassium phosphate monobasic | 25 | 25 |
| Potassium citrate monobasic | 5 | 5 |
| Magnesium sulfate | 0 | 0 |
| Magnesium chloride | 10 | 10 |
| D-(+)-Fructose | 2 | 2 |
| Glutathione reduced | 3 | 0 |
| Adenosine | 3 | 3 |
| Sodium hydroxide | 30 | 30 |
| Potassium hydroxide | 32.6 | 29 |
| Potassium | 180 | 180 |
| Sodium | 30 | 30 |
| Magnesium | 10 | 10 |
| Chloride | 20 | 20 |
| Sulfonic acid | 0 | 0 |

TABLE 6A-continued

Compositions of ROS 20 and 21 (used in FIG. 6)

|  | ROS-20 | ROS-21 |
|---|---|---|
| Osmolality (mOsm/Kg) | 339 | 333 |
| pH | 7.40 | 7.40 |

*all concentrations mM

TABLE 6B

Liver and kidney viability after 24 hours of cold preservation in ROS-20 or ROS-21 (evaluated by H&E staining; see FIG. 6)

|  | Na$^+$* | Cl$^-$ | Mg$^{2+}$ | SO$_4^{2-}$ | Glutathione (reduced) | Liver | Kidney |
|---|---|---|---|---|---|---|---|
| ROS-20 | 30 | 20 | 10 | 0 | 3 | 90% | 70% |
| ROS-21 | 30 | 20 | 10 | 0 | 0 | 70% | 50% |

*all concentrations mM

TABLE 7A

Figure 7:
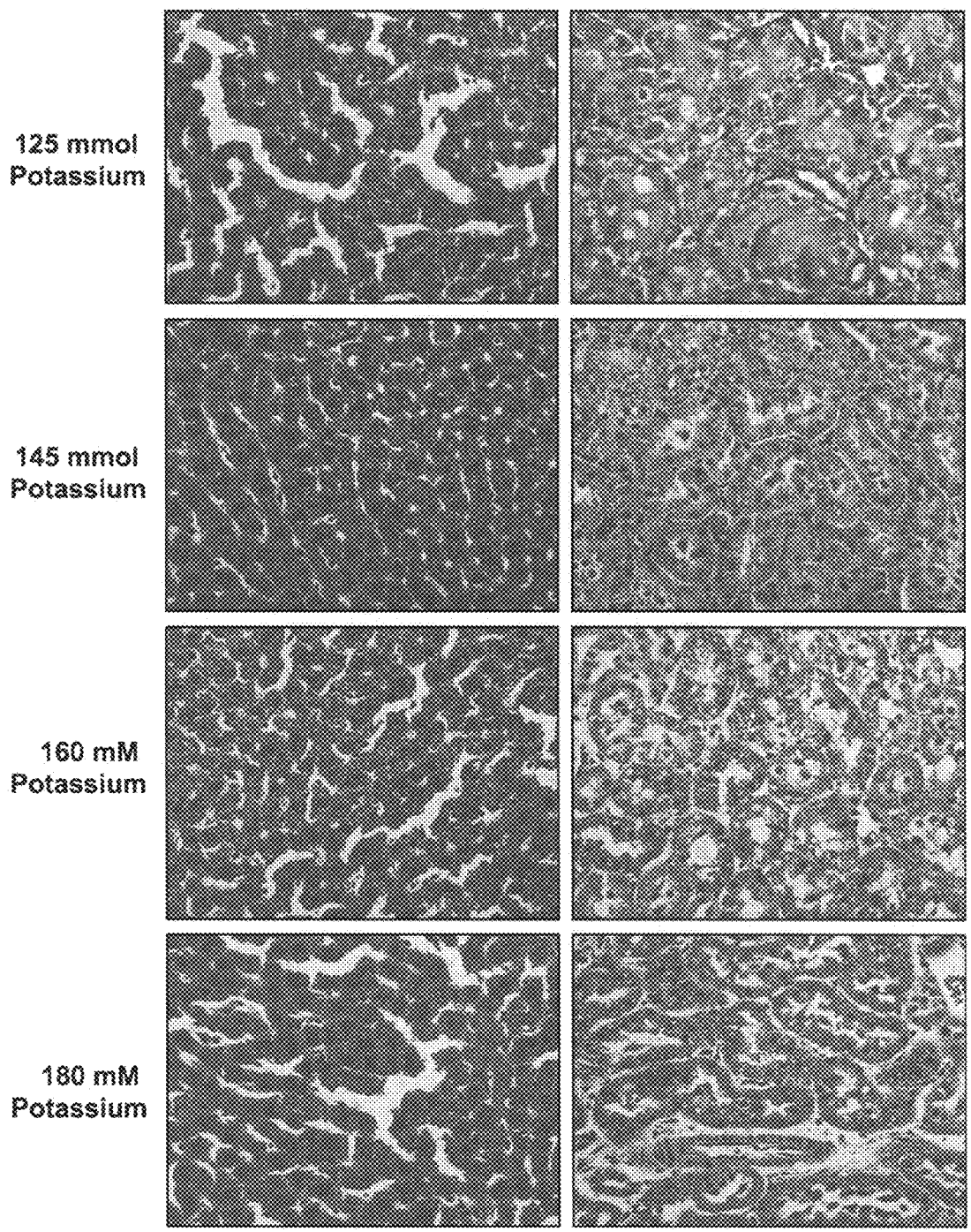
FIG. 7 is a series of pictures of rat liver and kidney tissue sections from a comparison study using ROS solutions 43, 45, 47, and 49, which contained the indicated concentrations of K+ ion. Samples were subjected to cold preservation for 48 hours and evaluated with H&E staining.

Compositions of ROS 43, 45, 47, and 49 (used in FIG. 7)

|  | ROS-43 | ROS-45 | ROS-47 | ROS-49 |
|---|---|---|---|---|
| Sorbitol* | 30 | 30 | 0 | 0 |
| Potassium D-gluconate | 52.4 | 72.4 | 67.4 | 87.4 |
| Saccharic acid potassium salt | 20 | 20 | 30 | 30 |
| Potassium phosphate monobasic | 25 | 25 | 25 | 25 |
| Potassium citrate monobasic | 5 | 5 | 5 | 5 |
| Magnesium sulfate | 0 | 0 | 0 | 0 |
| Magnesium chloride | 10 | 10 | 10 | 10 |
| D-(+)-Fructose | 5 | 5 | 5 | 5 |
| Glutathione reduced | 3 | 3 | 3 | 3 |
| Adenosine | 5 | 5 | 5 | 5 |
| Sodium hydroxide | 30 | 30 | 30 | 30 |
| Potassium hydroxide | 22.6 | 22.6 | 32.6 | 32.6 |
| Potassium | 125 | 145 | 160 | 180 |
| Sodium | 30 | 30 | 30 | 30 |
| Magnesium | 10 | 10 | 10 | 10 |
| Chloride | 20 | 20 | 20 | 20 |
| Sulfonic acid | 0 | 0 | 0 | 0 |
| Osmolality (mOsm/Kg) | 281 | 310 | 294 | 313 |
| pH | 7.40 | 7.40 | 7.40 | 7.40 |

*all concentrations mM

TABLE 7B

Liver and kidney viability after 48 hours of cold preservation in ROS-43, ROS-45, ROS-47, or ROS-49 (evaluated by H&E staining; see FIG. 7)

|  | Potassium* | Liver | Kidney |
|---|---|---|---|
| ROS-43 | 125 | 80% | 70% |
| ROS-45 | 145 | 90% | 80% |
| ROS-47 | 160 | 70% | 40% |
| ROS-49 | 180 | 70% | 60% |

*all concentrations mM

TABLE 8A

Figure 8:
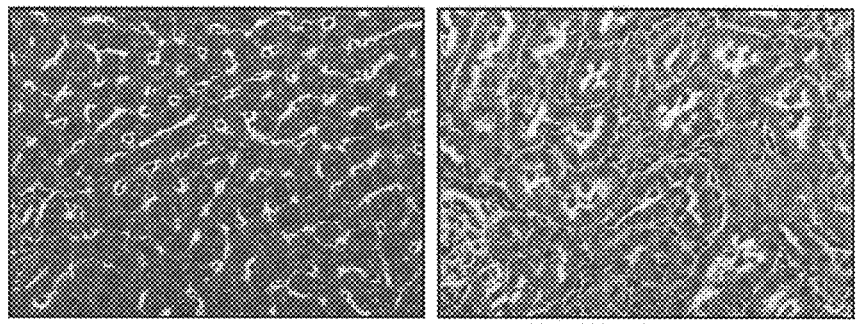
FIG. 8 is a series of pictures of rat liver and kidney tissue sections from a comparison study using ROS solutions containing different types of impermeants (saccharic acid vs. lactobionic acid). Samples were subjected to cold preservation for 48 hours and evaluated with H&E staining.
Figure 8:
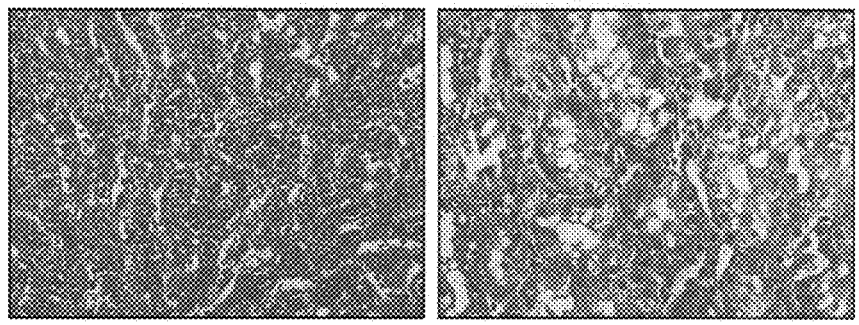

Compositions of ROS 45 and 53 (used in FIG. 8)

|  | ROS-45 | ROS-53 |
|---|---|---|
| Sorbitol* | 30 | 0 |
| Potassium D-gluconate | 72.4 | 92.4 |
| Saccharic acid potassium salt | 20 | 0 |
| Lactobionic acid | 0 | 20 |
| Potassium phosphate monobasic | 25 | 25 |
| Potassium citrate monobasic | 5 | 5 |
| Magnesium sulfate | 0 | 0 |
| Magnesium chloride | 10 | 10 |
| D-(+)-Fructose | 5 | 5 |
| Glutathione reduced | 3 | 3 |
| Adenosine | 5 | 5 |
| Sodium hydroxide | 30 | 30 |
| Potassium hydroxide | 22.6 | 22.6 |
| Potassium | 145 | 145 |
| Sodium | 30 | 30 |
| Magnesium | 10 | 10 |
| Chloride | 20 | 20 |
| Sulfonic acid | 0 | 0 |
| Osmolality (mOsm/Kg) | 310 | 293 |
| pH | 7.40 | 7.40 |

*all concentrations mM

TABLE 8B

Liver and kidney viability after 48 hours of cold preservation in ROS-45 or ROS-53 (evaluated by H&E staining; see FIG. 8)

|  | Impermeant | Liver | Kidney |
|---|---|---|---|
| ROS-45 | 20 mM saccharic acid | 90% | 80% |
| ROS-53 | 20 mM lactobionic acid | 70% | 50% |

The study depicted in FIG. 3 was performed to evaluate the effects of Na$^+$, Cl$^-$, Mg$^{2+}$, and SO$_4^{2-}$ concentrations on cell viability. As depicted in FIG. 3 and Table 3B, ROS-6 gave a better result than ROS-3, ROS-4, and ROS-5. For example, ROS-6 resulted in more intact sinusoid structure for liver samples, and more viable cells in the kidney cortex and medulla area. ROS-6 included Na$^+$, while ROS-3, ROS-4, and ROS-5 did not. In addition, when solutions having various SO$_4^{2-}$ ion concentrations were compared, solutions without SO$_4^{2-}$ ions but with Cl$^-$ ions (ROS-4 and ROS-6) resulted in greater cell viability than solutions containing SO$_4^{2-}$ ions but lacking Cl$^-$ ions (ROS-3 and ROS-5). These studies thus indicated that preservation solutions containing Na$^+$ and Cl$^-$, without SO$_4^{2-}$, are beneficial for maintaining cellular membrane stability and viability.

Additional experiments were conducted to further evaluate the effects of Na$^+$, Cl$^-$, Mg$^{2+}$, and SO$_4^{2-}$ concentrations on cell viability. Results are depicted in Table 4B and FIG. 4 for ROS-8, ROS-9, and ROS-10, which have the same concentration (14 mM) of Mg$^{2+}$ ions, decreasing concentrations of Na$^+$ and Cl$^-$, and increasing concentrations of SO$_4^{2-}$. ROS-8, which had the greatest concentrations of Na$^+$ and Cl$^-$ and the lowest concentration of SO$_4^{2-}$, resulted in the most intact sinusoid structure for liver samples greater viability in the kidney cortex and medulla areas.

FIG. 5 and Table 5A show the results of experiments using ROS-14, ROS-16, ROS-18, and ROS-20, which contained increasing concentrations of Na$^+$, Cl$^-$, and Mg$^{2+}$, and varying concentrations of SO$_4^{2-}$. The solution containing 5 mM Mg$^{2+}$ (ROS-14) was not optimal for maintaining the sinusoid structure of liver or kidney. Tissues incubated in ROS-16 also exhibited broken sinusoid structures in both liver and kidney cortex and medullar areas, indicating that increasing the concentration of Mg$^{2+}$ ions to 10 mM did not inhibit cellular damage when 5 mM SO$_4^{2-}$ was present. When compared with ROS-14 and ROS-16 with respect to kidney viability, a solution without SO$_4^{2-}$ (ROS-20) gave better results.

Improved cell viability also was observed when the $SO_4^{2-}$ ion was decreased to 3 mM and $Na^+$ and $Cl^-$ ion concentrations were increased, as in ROS-18. The best result with respect to liver and kidney viability in these experiments, however, was achieved with ROS-20, which contained no $SO_4^{2-}$ and increased $Na^+$ (30 mM) and $Cl^-$ (20 mM) ion concentrations.

To determine the role of antioxidant (glutathione) in maintaining cell viability and membrane stability, experiments were conducted using ROS-20 and ROS-21 for cold organ storage. Data are shown in FIG. 6 and Table 6B. When 3 mM glutathione was present, sinusoid structures were maintained and cell viability was high. Without glutathione, sinusoid structures were torn and viability was reduced.

Solutions containing increasing concentrations of potassium also were examined. Data are presented in FIG. 7 and Table 7B. Solutions containing 125, 160, or 180 mM potassium ion resulted in significant damage to cortex and medulla (kidney) and sinusoid (liver) structure. Cell viability was 80% for liver and 70% for kidney after 48 hours of cold storage in ROS-43, which contained 125 mM potassium ion—similar to UW solution. Viability was 70% for liver and 60% for kidney with ROS-49, which contained 180 mM potassium ion. Viability was decreased to 30% for liver and 20% for kidney when a solution containing a higher concentration (195 mM) of potassium ion was used. In addition, sinusoid structure was completely broken, as were cell to cell interactions. The best tissue viability (90% for liver and 80% for kidney) was achieved using ROS-45, which contained 145 mM potassium ion.

To determine the effect of different saccharides on cell viability and membrane stability, ROS-45 and ROS-53 solutions were compared. Results are shown in FIG. 8 and Table 8B. The solution containing saccharic acid (ROS-45) resulted in healthy sinusoid structures. In contrast, loss of cytoplasm in liver samples and cellular damage to the cortex and medullar areas of kidney samples was observed with ROS-53, which contained lactobionic acid. Thus, it appears that monosaccharic acids are better than disaccharides for maintaining cell membrane stability and integrity.

Taken together, the above results indicate the following:
- Solutions containing less than 140 mM potassium or more than 180 mM potassium are insufficient to maintain metabolic viability of the cells.
- Solutions containing less than 20 mM sodium or more than 40 mM sodium are insufficient to maintain metabolic function and cell viability.
- Solutions containing less than 8 mM magnesium or more than 12 mM magnesium are insufficient to maintain metabolic function and cell viability.
- Solutions containing less than 16 mM chloride or more than 24 mM chloride are insufficient to maintain metabolic function and cell viability.
- Solutions containing less than 1 mM glutathione or more than 6 mM glutathione are insufficient to maintain metabolic function and cell viability.
- Solutions containing less than 3 mM adenosine or more than 7 mM adenosine are insufficient to maintain metabolic function and cell viability.
- Solutions without magnesium sulfate result in good organ viability and cell integrity as compared with solutions containing magnesium sulfate.
- Solutions containing saccharic acid as an impermeant result in improved organ viability and cell integrity as compared to solutions containing lactobionic acid as an impermeant.
- Magnesium should be supplied by magnesium chloride, as use of magnesium sulfonate leads to reduced cell viability.

Overall, preservation solutions containing 5 to 40 mM sorbitol, 50 to 120 mM potassium D-gluconate, 10 to 40 mM D-saccharic acid, potassium salt, 15 to 30 mM potassium phosphate, monobasic, 3 to 12 mM potassium citrate, monobasic, 8 to 12 mM magnesium chloride, 2 to 7 mM D-(+)-fructose, 1 to 6 mM glutathione (reduced), 3 to 7 mM adenosine, 20 to 40 mM sodium hydroxide, 10 to 40 mM potassium hydroxide, 140 to 180 mEq/L potassium, 20 to 40 mEq/L sodium, 8 to 12 mEq/L magnesium, 16 to 24 mEq/L chloride, and 0 mEq/L sulfate, and having pH 7.3 to 7.5 and osmolality 290 to 360 mOsm/Kg, were deemed to be optimal for maintaining the metabolic function and viability of organs and tissues, presumably due to maintenance of plasma membrane integrity, as well as mitochondrial and nuclear membrane integrity, to degrees comparable to those observed under normal conditions. Such solutions can permit cold preservation of organs and tissues for periods up to about 72 hours, or even longer.

Example 2

Comparison of UW Solution and Thermo-ROS

Rat livers and kidneys were placed in UW solution or Thermo-ROS solution and maintained at 0 to 1° C. for up to three days. Tissue viability was measured at days 0, 1, and 3. Results are shown in Table 9 and FIG. 9 for one day (24 hours) and three days (72 hours) of preservation. Tissue viability was evaluated with H&E staining.

TABLE 9

Comparison study of UW solution vs. Thermo-ROS

|  | Day 0 | Day 1 | Day 3 |
| --- | --- | --- | --- |
| UW solution | | | |
| Liver | 70% | 60% | 20% |
| Kidney | 70% | 50% | 20% |
| Thermo-ROS | | | |
| Liver | 100% | 100% | 80% |
| Kidney | 90% | 80% | 40% |

Figure 9:
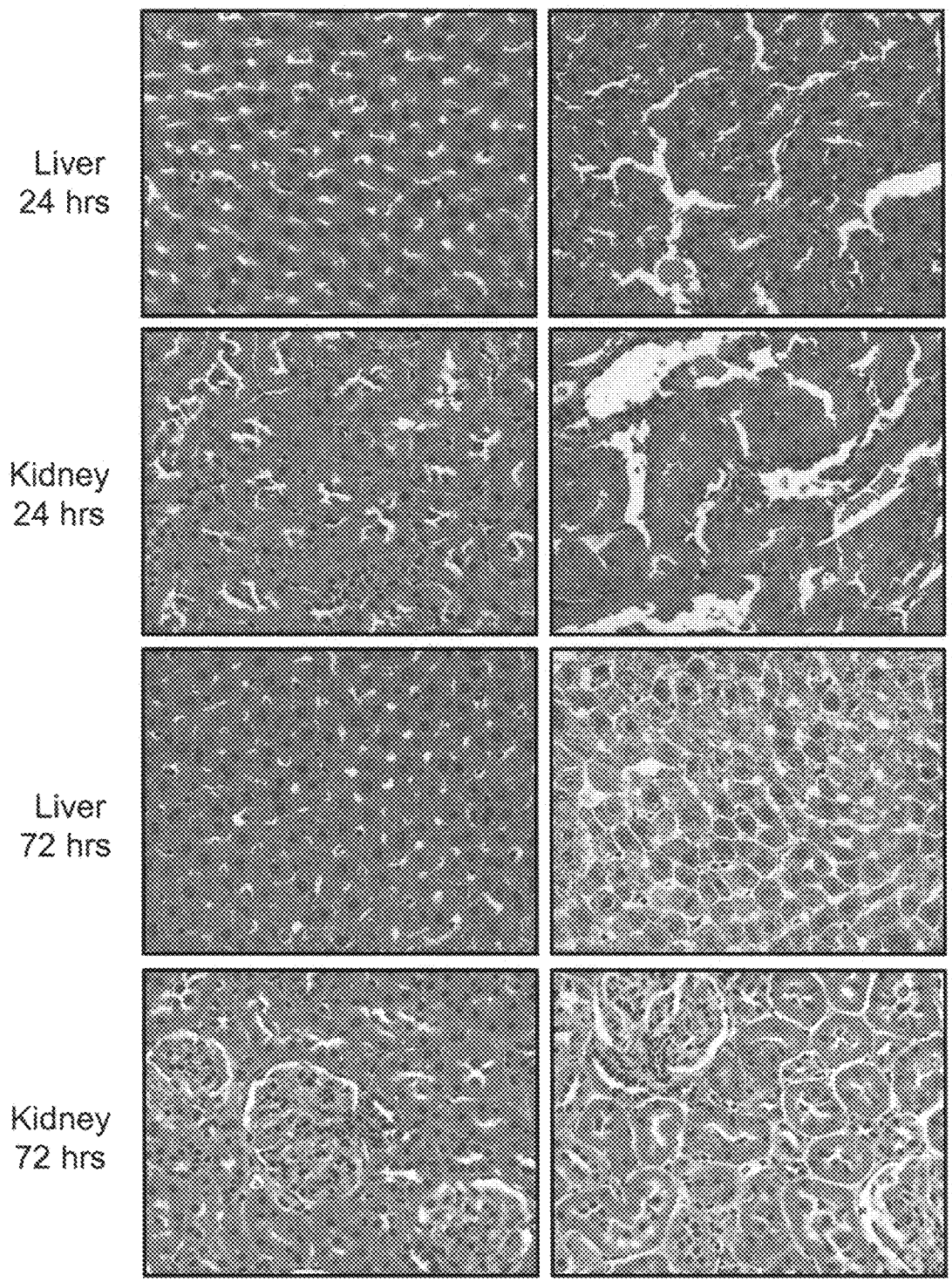
FIG. 9 is a series of pictures of rat liver and kidney tissue sections subjected to preservation with UW or Thermo-ROS for 24 or 72 hours, as indicated, before evaluation with H&E staining.

The data presented in Table 9 and FIG. 9 show that as compared to UW solution, Thermo-ROS resulted in improved organ viability after cold preservation of rat liver and kidney at both 24 and 72 hours. These results indicate that optimal concentrations of potassium, sodium, chloride, magnesium, glutathione, fructose, and adenosine can maintain metabolic function and organ/tissue viability, presumably due to maintaining plasma membrane integrity to a degree that is essentially the same as that observed under normal conditions.

Example 3

Electron Microscopy Evaluation

Figure 10:
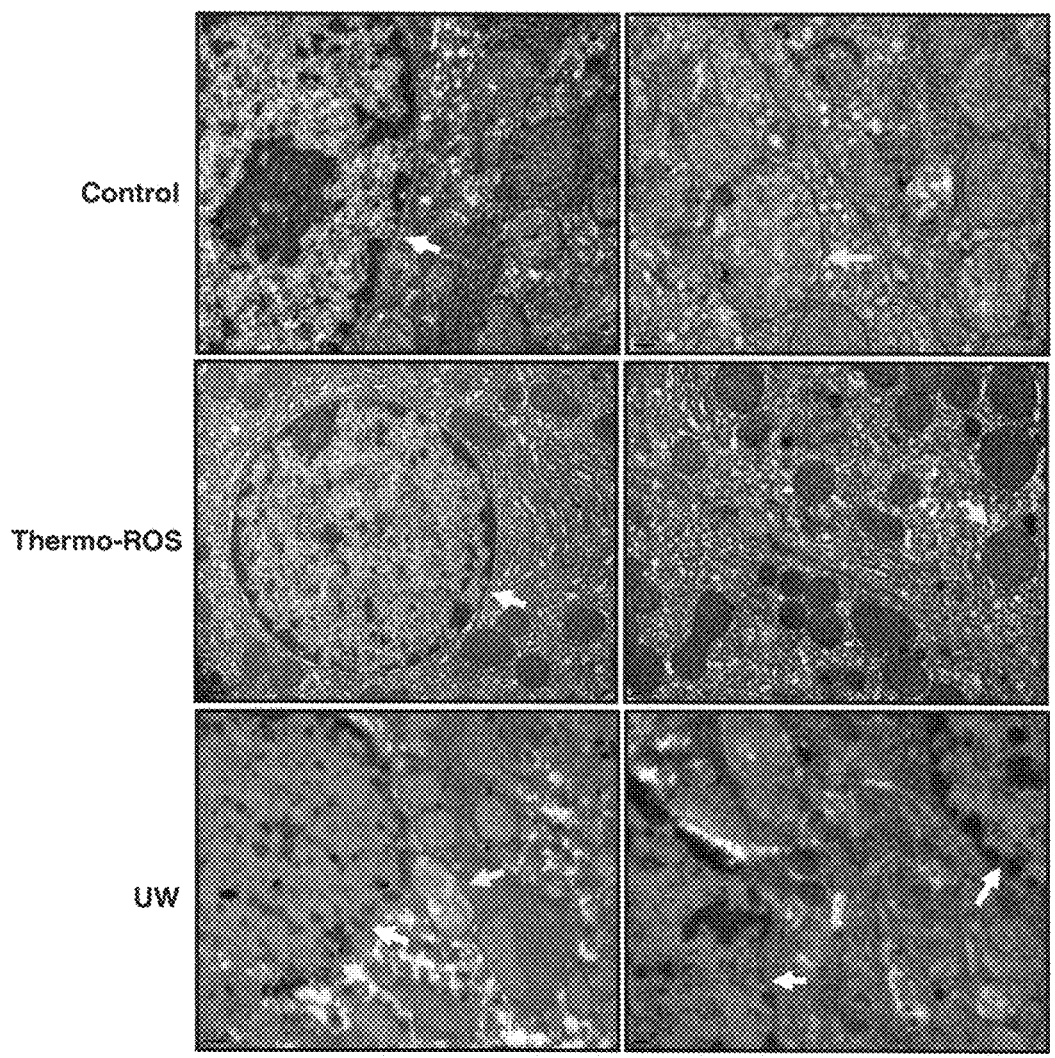
FIG. 10 is a series of electron microscopy images of rat liver tissue sections stored in Thermo-ROS (middle panels) vs. UW solution (bottom panels) for 24 hours. Controls (top panels) represent unpreserved samples. White arrows, nuclear membrane; yellow arrows, mitochondrial membrane; red arrows, plasma membrane.

Rat livers were placed in Thermo-ROS or UW solution for 24 hours, and then fixed with 2.5% glutaraldehyde. Non-preserved liver samples were used as controls. Specimens were prepared from fixed tissues, and membrane integrity was evaluated with TEM. The data presented in FIG. 10 show that Thermo-ROS was quite beneficial for maintaining cellular plasma, nuclear, and mitochondrial membrane integrity, and was better than UW solution for cold preservation for 24 hours. Thus, optimal concentrations of potassium, sodium, chloride, magnesium ion, glutathione, and adenosine contribute to maintaining plasma membrane integrity, such that the membranes appear similar to those observed under normal conditions. This can permit cold preservation of organs and tissues for periods up to at least 72 hours.

Example 4

Rat Kidney Transplant Survival in vivo-UW vs. Thermo-ROS

A small animal (rat) kidney transplant survival in vivo study was conducted as described above to further compare UW solution and Thermo-ROS. Results are shown in Table 10.

TABLE 10

Survival of rats receiving kidneys stored in UW solution vs. kidneys stored in Thermo-ROS solution

| | UW solution | Thermo-ROS |
|---|---|---|
| Quantity | n = 2 | n = 2 |
| Storage time | ~34 hours | ~37 hours |
| Survival (hours) | #1—died immediately<br>#2—died 18 h after transplant | #3—died 24 h after transplant<br>#4—survived until euthanized (4 days) |
| Blood urea nitrogen | N/A | 25 mg/dL (#4 rat)<br>(Reference range: 9~30) |
| Creatinine | N/A | 0.5 mg/dL (#4 rat)<br>(Reference range: 0.5~2.2) |
| Cause of death | Graft rejection (#1, #2 rat) | Bacterial infection (#3 rat)<br>No rejection (#4 rat) |

As indicated in Table 10, when UW solution was used, both recipient rats died within 18 hours. Autopsies showed that the cortex and medullar areas of these donor kidneys were completely broken. Further, coagulated blood was observed on the donor kidneys, and blood leakage to the ureter and bladder of recipient rats also was observed, indicating that total malfunction of the donor kidneys was a cause of death for the recipient rats. In contrast, transplanting kidneys stored with Thermo-ROS gave better results. Although one recipient died within 24 hours after transplant, autopsy showed many white blood cells in the lung, indicating that the rat died from a bacterial infection such as septic shock. The other rat, which displayed a healthy status until day 4, was euthanized in order to evaluate physiological indicators of the donor kidney, such as blood urea nitrogen and creatinine. Both were within normal range. Thus, Thermo-ROS is a more relevant and useful organ preservation solution than the commercial UW solution.

Example 5

Cryo Preservation

Figure 11:
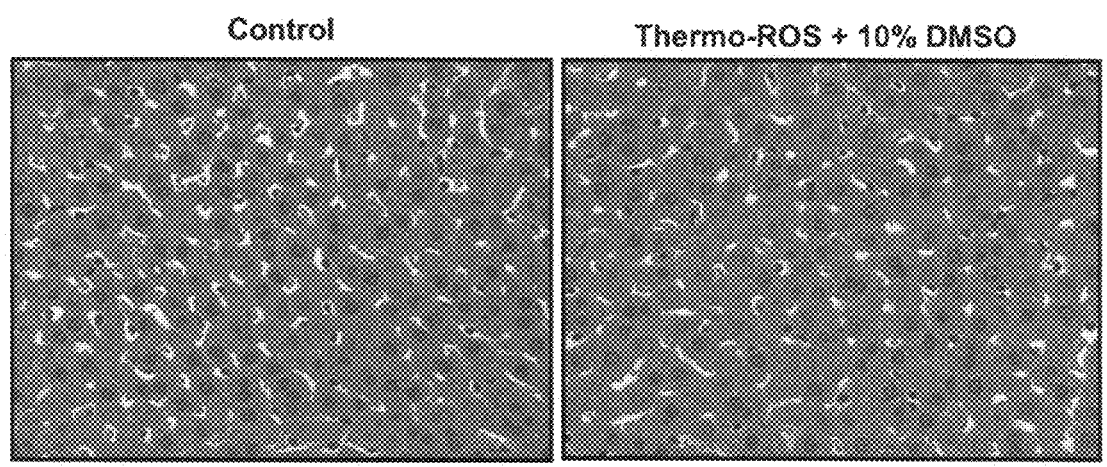
FIG. 11 is a pair of pictures showing tissue sections from a control rat liver (left panel) and from a rat liver subjected to cryo preservation with ROS+10 percent DMSO at −20° C. for 3 days (right panel).

Rat livers were placed in Thermo-ROS solution containing 10% dimethyl sulfoxide (DMSO), and stored at −20° C. for three days (72 hours). After cryopreservation, organs were quickly defrosted at room temperature, fixed with a 10% formalin solution, and evaluated by H&E staining. Results are shown in Table 11 and FIG. 11. These data indicate that cryopreservation in Thermo-ROS+10% DMSO results in good organ viability and integrity.

TABLE 11

Evaluation of rat liver viability with Thermo-ROS solution + 10% DMSO after cryo preservation for 3 days

| | Day 0 | Day 3 |
|---|---|---|
| Thermo-ROS + 10% DMSO | 100% | 80% |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   5 to 40 mM sorbitol;
   50 to 120 mM potassium D-gluconate;
   10 to 40 mM D-saccharic acid potassium salt,
   15 to 30 mM potassium phosphate monobasic;
   3 to 12 mM potassium citrate monobasic;
   8 to 12 mM magnesium chloride;
   2 to 7 mM D-(+)-fructose;
   1 to 6 mM glutathione reduced;
   3 to 7 mM adenosine;
   20 to 40 mM sodium hydroxide;
   10 to 40 mM potassium hydroxide;
   wherein the composition contains a total of
   140 to 180 mEq/L potassium ion;
   20 to 40 mEq/L sodium ion;
   8 to 12 mq/L magnesium ion;
   16 to 24 mEq/L chloride ion, and wherein
   the composition has a pH of 7.3 to 7.5 and an osmolality of 290 to 360 mOsm/Kg.

2. The composition of claim 1, comprising 145 mEq/L potassium ion.

3. The composition of claim 2, comprising sodium ion and chloride ion at a ratio of 3:2 sodium ion: chloride ion.

4. The composition of claim 2, comprising 10 mM magnesium chloride.

5. The composition of claim 1, wherein the composition comprises no sulfate ion.

6. The composition of claim 1, further comprising 10% dimethyl sulfoxide (DMSO).

7. The composition of claim 1, further comprising 1 to 5 percent hydroxyethylstarch.

8. A composition comprising:
   30 mM sorbitol;
   73 mM potassium D-gluconate;
   20 mM D-saccharic acid potassium salt,
   25 mM potassium phosphate monobasic;
   5 mM potassium citrate monobasic;
   10 mM magnesium chloride;
   5 mM D-(+)-fructose;
   3 mM glutathione reduced;
   5 mM adenosine;
   30 mM sodium hydroxide;
   23 mM potassium hydroxide;
   wherein the composition contains a total of
   145 mEq/L potassium ion;
   30 mEq/L sodium ion;
   10 mq/L magnesium ion;
   20 mEq/L chloride ion, and wherein the composition has a pH of 7.4 and an osmolality of 320 mOsm/Kg.

9. The composition of claim 8, further comprising 10% DMSO.

10. A method for preserving a cell, comprising contacting the cell with the composition of claim 1, and placing the cell at a temperature of 0 to 1° C.

11. The method of claim 10, further comprising storing the cell at 0 to 1° C. for up to 72 hours.

12. The method of claim 10, wherein the cell is a liver, kidney, spleen, pancreas, heart, lung, small bowel, eye, or skin cell.

13. The method of claim 10, wherein the cell is within a liver, kidney, spleen, pancreas, heart, lung, small bowel section, eye, or skin section.

14. The method of claim 10, wherein the cell is a mammalian cell.

15. The method of claim 10, wherein the cell is a human cell.

16. The method of claim 10, wherein the composition is the composition of claim 6.

17. A method for cryopreserving a cell, comprising contacting the cell with the composition of claim 6 or 9 and placing the cell at a temperature of about −196° C.

18. The method of claim 17, further comprising storing the cell at −196° C. for up to two years.

19. The method of claim 17, wherein the cell is a liver, kidney, spleen, pancreas, heart, lung, small bowel, eye, or skin cell.

20. The method of claim 17, wherein the cell is within a liver, kidney, spleen, pancreas, heart, lung, small bowel section, eye, or skin section.

21. The method of claim 17, wherein the cell is a mammalian cell.

22. The method of claim 17, wherein the cell is a human cell.

* * * * *